United States Patent [19]
Yam et al.

[11] Patent Number: 6,024,120
[45] Date of Patent: Feb. 15, 2000

[54] PRESSURE RELIEF VALVE WITH MOVING DIAPHRAGM

[75] Inventors: Jacky S. Yam, St. Louis; Eugene E. Weilbacher, Ellisville, both of Mo.

[73] Assignee: Sherwood Services AG, Schaffhausen, Switzerland

[21] Appl. No.: 09/161,031

[22] Filed: Sep. 25, 1998

[51] Int. Cl.[7] .................................................. F16K 31/14
[52] U.S. Cl. .......................... 137/495; 137/205; 137/508; 137/907; 604/118; 604/119; 604/121; 604/319; 604/321; 128/204.26; 128/205.24
[58] Field of Search ..................................... 137/495, 508, 137/907, 205, 908; 604/117, 118, 119, 121, 129, 324, 321; 128/204.26, 205.24

[56] References Cited

U.S. PATENT DOCUMENTS

| | | | |
|---|---|---|---|
| 4,372,336 | 2/1983 | Cornell et al. | 137/205 |
| 4,605,400 | 8/1986 | Kurtz et al. | 604/319 |
| 4,768,542 | 9/1988 | Morris | 137/495 |
| 5,634,494 | 6/1997 | Martens | 137/205 |
| 5,871,027 | 2/1999 | Shimizu et al. | 137/205 |

*Primary Examiner*—Henry J. Recla
*Assistant Examiner*—Khoa Huynh
*Attorney, Agent, or Firm*—Mark S. Leonardo; Brown, Rudnick, Freed & Gesmer, P.C.

[57] ABSTRACT

A valve for relieving an excess negative pressure condition inside a medical device comprising a diaphragm with an inner periphery and an outer periphery and an actuator having a piston extending axially therefrom which is inserted through the inner periphery of the diaphragm. The piston comprises a plurality of legs that form a void therebetween at the free end thereof. The outer periphery of the diaphragm is sandwiched between the upper and lower housings so as to create a hermetic seal that separates the valve into a venting side and a suction side. To relieve an excess negative pressure condition the diaphragm is operable in one of two positions. In the first position, a biasing members forces the inner periphery of the diaphragm in sealing engagement around the circumference of the piston so that a hermetic seal is maintained between the suction side and the venting side. When negative pressure inside the medical device begins to rise, the inner periphery of the diaphragm moves in sealing engagement along the piston so that a constant sealing force is applied around the circumference of the piston until it reaches the plurality of legs at the free end thereof. As the inner periphery moves over the plurality of legs, the void establishes communication with both the suction side and the venting side, thereby permitting ambient air to vent into the suction side and lower the negative pressure therein.

34 Claims, 12 Drawing Sheets figure 2 figure 3 figure 4 figure 5 figure 6 figure 7 figure 8 figure 9 figure 10 figure 11 figure 12 figure 13 figure 14

PRESSURE RELIEF VALVE WITH MOVING DIAPHRAGM

BACKGROUND OF THE INVENTION

1. Field of the Invention

This invention relates generally to a method and apparatus for relieving an excess negative pressure condition, and in particular to a negative pressure relief valve for automatically or manually relieving an excess negative pressure condition in a medical device. Specifically, the invention relates to a combination automatic/manual negative pressure relief valve having a moving diaphragm that permits ambient air to enter the suction side of the valve when negative pressure therein exceeds a predetermined threshold in order to relieve an excess negative pressure condition inside the medical device.

2. Prior Art

Negative pressure relief valves are well known in the medical art. Typically, such valves are incorporated in medical devices, such a chest drainage units (CDU), in order to protect the patient from possible tissue damage in the pleural cavity caused by an excess negative pressure condition generated inside the CDU. To protect the patient a negative pressure relief valve is sometimes housed on the outer wall of the CDU for permitting the venting in of ambient air in order to relieve an excess negative pressure that may build inside the CDU during operation.

A CDU is an apparatus for suctioning gases and liquids from the pleural cavity of a patient. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various infections can cause a build up of liquid and gases around the lungs in the intrapleural space. When this happens, it causes the lungs to collapse to a volume much less than that of the pleural cavity, thereby severely impairing breathing functions of the patient. The lungs can be re-expanded to their normal state to fill the pleural cavity by draining the liquid and gases from the intrapleural space using a medical device like a CDU. A typical CDU and its operation is disclosed in U.S. patent application Ser. No. 08/810,056 to Swisher et al. entitled "Chest Drainage Unit with Controlled Automatic Excess Negativity Relief Feature" and is herein incorporated by reference in its entirety. However, any kind of medical device that requires low negative pressure control, such as a Tracheo Gas Insufflation (TGI) Device, is felt to fall within the scope of the present invention.

During the suctioning of liquids and gases from the pleural cavity of a patient by the CDU, negative pressure inside the CDU can build up to dangerous levels due to excess vacuum being mistakenly applied to the CDU from a hospital vacuum source by a user or when a procedure called "milking" is performed to the transfer tubing attached to the CDU. "Milking" is accomplished by squeezing the portion of latex transfer tubing between the patient and the CDU adjacent the patient and running the fingers down along the tube toward the CDU. When the tube is thereafter released, in the absence of any venting of the CDU's collection chamber, a relatively high level of negative pressure will be reflected in the patient's pleural cavity causing the patient's tissue around the end of the catheter in the pleural cavity to be sucked into the holes of the catheter, thereby causing irritation and tissue damage.

Negative pressure relief valves are used as a safety mechanism for ensuring that negative pressure inside the CDU does not rise to dangerous levels. One type of prior art valve is disclosed in U.S. Pat. No. 4,372,336 to Cornell et al. entitled "Chest Drainage Unit". The valve disclosed in Cornell et al. is a manual relief valve that permits venting of the CDU's collection chamber by simply depressing a button located on the top portion of the valve for venting in atmospheric air into the CDU and lowering the negative pressure therein. However, the valve disclosed by Cornell et al. lacks any type of automatic feature that would permit excess negative pressure inside the CDU to be relieved automatically without manual intervention.

U.S. Pat. No. 4,605,400 to Kurtz et al. entitled "Surgical Drainage Apparatus" discloses an automatic excess negative pressure relief valve that automatically lowers excess negative pressure. The Kurtz et al. device is an adjustable umbrella valve that automatically opens to vent in ambient air into the CDU when negative pressure therein reaches a predetermined calibration point set for a biasing means. The biasing means, for example a helical spring, maintains the umbrella valve in a sealed position until the negative pressure inside the CDU reaches the calibration point. When the calibration point is reached, the pressure exerted by the ambient air overcomes the force applied by the biasing means to the valve, thereby opening the valve to atmosphere. As ambient air is allowed to bleed into the device it gradually lowers the negative pressure inside the CDU until it falls below the calibration point, whereupon the valve is again closed off to the inflow of ambient air into the CDU.

Unfortunately, the Kurtz et al. valve suffers from several drawbacks. As negative pressure inside the CDU nears the calibration point set for the valve, the Kurtz et al. device may begin to bleed in ambient air, thereby prematurely lowering the pressure inside the CDU. For example, an umbrella-type valve similar to that disclosed by Kurtz et al. may begin to prematurely leak and vent in ambient air as the umbrella valve begins to momentarily unseat, even though the negative pressure inside the CDU has not yet reached the set calibration point. Thus, the prior art umbrella valve may sometimes exhibit leakage which is undesirable. Moreover, the Kurtz et al. device lacks a combined valve that combines both an automatic means as well as a manual means of relieving an excess negative pressure condition inside the CDU.

An improvement on the above-noted umbrella valve is the use of a resilient diaphragm that hermetically separates the CDU into a venting side and a suction side. The suction side is the interior portions of the CDU and valve that are maintained at some negative pressure value while the venting side is that portion of the valve that is open to atmosphere. The diaphragm comprises an outer periphery and an inner periphery, wherein the inner periphery forms of the diaphragm is integrally attached or formed to a proximal end of a stem which is connected to a valve seat. The valve seat is normally seated and sealed against an opening that separates the venting side from the suction side, thereby preventing the inflow of ambient air into the suction side. A biasing means, for example a helical spring, biases the diaphragm so that the valve seat is seated against the opening. When the negative pressure inside the CDU rises and then exceeds the calibration point set for the biasing means, the biasing means begins to exert a specific pressure against the diaphragm in proportion to the amount of negative pressure generated in the suction side of the apparatus, thereby causing the diaphragm to flex. As the diaphragm flexes, it concurrently causes the stem to move in a direction that unseats the valve seat from the opening. Once the opening is unblocked it permits ambient air to flow from the venting side into the suction side, thus lowering the negative pressure inside the device. As negative pressure falls below the above-noted calibration point, the biasing means moves the diaphragm in a direction that forces the valve seat against the opening and closes it to fluid flow communication therethrough. However, this type of diaphragm valve also suffers from leakage since the valve seat configuration does not maintain a constant sealing force against the opening as the negative pressure inside the CDU nears the calibration point. Instead, the sealing force applied by the valve seat begins to drop off before the calibration point is reached, thereby permitting ambient air to prematurely vent into the suction side of the CDU.

As of yet, nothing in the prior art has addressed the problem of developing an excess negative pressure relief valve that prevents the leakage of ambient air through the valve mechanism when negative pressure inside the device has not reached or exceeded the calibration point set for the valve. Moreover, nothing in the prior art has addressed the need for an improved means of automatically actuating an excess negative pressure relief valve whereby the sealing force remains constant until the calibration point set for the biasing means is reached.

OBJECTS AND SUMMARY OF THE INVENTION

The principle object of the present invention is to provide a valve for automatically relieving excess negative pressure.

A further object of the present invention is to provide a valve that includes a sealing means that maintains a constant sealing force until the calibration point set for actuating the valve is reached.

Another principle object of the present invention is to provide a combined means for automatically and manually relieving an excess negative pressure inside a medical device.

Another further principle object of the present invention is to provide an efficient and improved means for relieving an excess negative pressure condition in a medical device.

Another important object of the present invention is to provide a valve that does not exhibit leakage or premature venting in of ambient air when negative pressure has not reached or exceeded the calibration point set for actuating the valve.

These and other objects of the present invention are realized in the preferred embodiment of the present inventions described by way of example and not by way of limitation. The preferred embodiment provides for a combination automatic/manual negative pressure relief valve disposed on the outer wall of a medical device and comprises an upper housing and an attachable lower housing. The upper housing includes an internally threaded top section with an open top and a radially wider lower section that houses a resilient diaphragm and a retainer. Disposed inside and engaged to the threaded top section is an actuating body that includes an outer threaded top part that forms a cavity therethrough and a piston which axially extends away from the lower base of the outer threaded top part. The piston includes a solid piston rod at its proximal end that is attached to, or integrally formed with, the lower base of the outer threaded top part and a plurality of legs that form a void therebetween at the free distal end of the piston. The lower housing includes a biasing means for biasing the diaphragm that seals the valve from fluid flow communication therethrough, a filter for filtering incoming ambient air, and a vent for venting through ambient air. The biasing means has a set calibration point wherein when negative pressure inside the medical device is below the value set for the calibration point the biasing means exerts a sufficient force against the diaphragm through which closes the valve to fluid flow therethrough.

The diaphragm is manufactured from a flexible resilient material that forms an outer periphery in coaxial alignment with an inner periphery. The outer periphery is sandwiched between the upper and the lower housing so as to create a hermetic seal while the inner periphery forms an axial opening that is adapted to receive the piston therethrough. The diaphragm is engaged to the piston in a first position by a biasing means that applies a predetermined force against the diaphragm so that the inner periphery is sealingly engaged around the circumference of the piston rod at the proximal end of the piston. In the first position, the diaphragm hermetically separates the valve into a venting side and a suction side. When negative pressure in the suction side of the valve begins to near the calibration point set for a biasing means, pressure exerted by ambient air on the venting side begins to the inner periphery air on the venting side begins to push the inner periphery of the diaphragm axially along the piston from the proximal end of the piston toward the distal end thereof. As the inner periphery moves along the piston it maintains a constant sealing force around the circumference of the piston rod until the inner periphery reaches the plurality of legs formed at the distal end of the piston. In the second position, negative pressure inside the medical device reaches the calibration point so that the inner periphery of the diaphragm moves over the plurality of legs and the void formed therebetween communicates with both the venting side and the suction side of the valve. As the void communicates with both sides of the valve ambient air is allowed to flow from the venting side to the suction side of the valve through the void, thereby lowering the negative pressure inside the medical device and eliminating the excess negative pressure condition therein.

Once negative pressure on the suction side falls below the calibration point, the inner periphery of the diaphragm moves back up and reseals itself around the circumference of the piston rod, so that fluid flow communication between the suction side and the venting side is once again closed. In manual operation, a push cap is provided with a means for manually pressing down on the diaphragm and overcome the force applied by the biasing means against the diaphragm so that the inner periphery of the diaphragm moves from the first "closed" position to the second "open" position as discussed above. The manual depression of the push cap thus lowers negative pressure inside the medical device until the push cap is released by the user. Upon release of the push cap, the diaphragm returns to the first position, thereby preventing the further entry of ambient air into the suction side of the CDU and closing the valve to fluid flow therethrough.

DETAILED DESCRIPTION OF THE INVENTION

Figure 1:
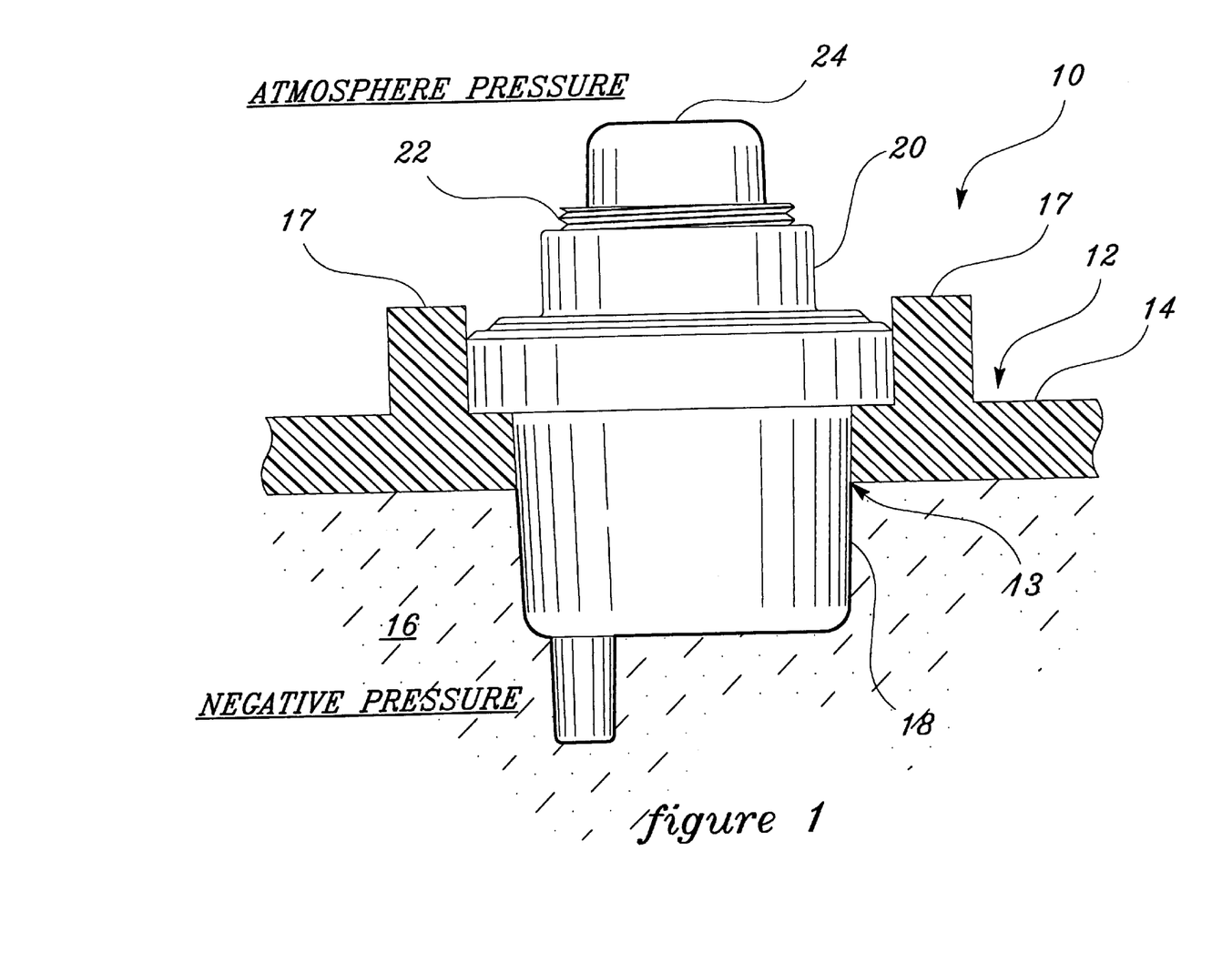
FIG. 1 is a side view of the preferred embodiment of the negative pressure relief valve seated in the wall of a medical device according to the present invention.

Referring to the drawings, the preferred embodiment of the negative pressure relief valve of the present invention is illustrated and generally indicated as 10 in FIG. 1. As shown in FIG. 1, valve 10 is hermetically attached to an annular-shaped outlet 13 formed through an outer wall 14 of a medical device, for example a Chest Drainage Unit (CDU) 12. CDU 12 is an apparatus for draining gases and liquids from the pleural cavity of patient. A typical CDU which incorporates valve 10 is disclosed in U.S. patent application Ser. No. 08/810,056 entitled "Chest Drainage Unit with Controlled Automatic Excess Negativity Relief Feature" and is herein incorporated by reference in its entirety.

Valve 10 comprises an upper housing 20 integrally formed with or attached to a lower housing 18. Upper housing 20 is seated against an annular retaining ridge 17 formed on an outer wall 14 that forms a part of a collection chamber 16 of CDU 12. The collection chamber 16 is the collection site for fluids drawn from a patient pleural cavity. Fluid drawn from a patient's pleural cavity enter the collection chamber 16 through an outlet (not shown) and collect therein until reinfused back to the patient. In order to draw fluids into the CDU 12, the collection chamber 16 is maintained at a predetermined negative pressure by attaching the CDU 12 to a source of vacuum. Thus, the upper housing 20 is exposed to ambient pressure while the lower housing 18 is exposed to negative pressure. Preferably, lower housing 18 is ultrasonically welded to the upper housing 20, although other alternative methods of coupling the two housings 18 and 20, such as bonding with an adhesive, snap fit or an interference fit is felt to fall within the scope of the resent invention.

Figure 2:
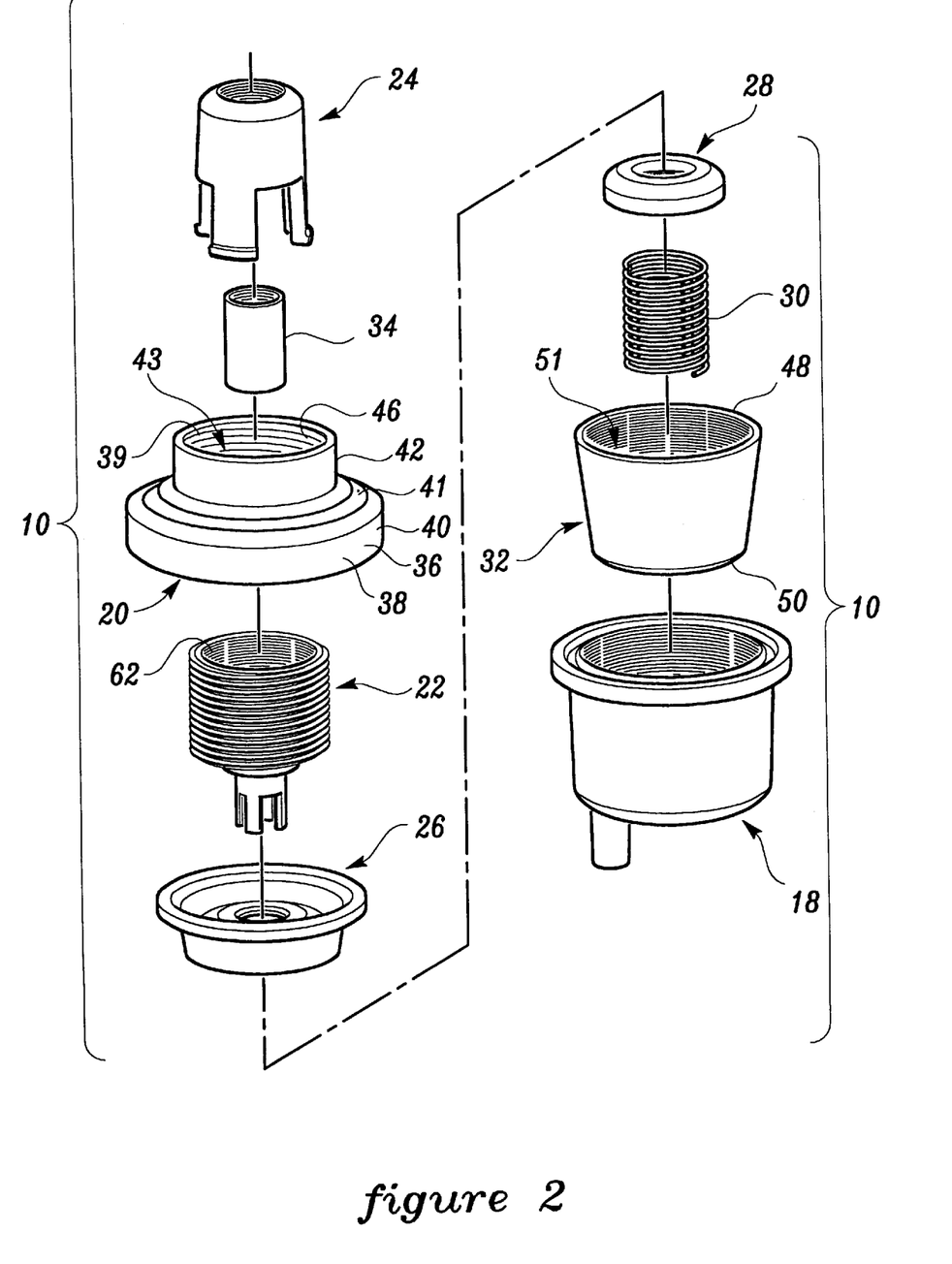
FIG. 2 is an exploded view of the negative pressure relief valve showing the constituent components according to the present invention.

As shown in greater detail in FIG. 2, upper housing 20 has an annular-shaped upper portion 42 that forms an interior upper cavity 43 having a threaded portion 46. Extending radially outward from upper portion 42 and in co-axial alignment therewith is an annular-shaped lower portion 40 which forms a plurality of stepped ridges 41 that terminate in a flange 36. The stepped ridges 41 and flange 36 form an interior lower cavity 38 that is in communication with the upper cavity 43. Disposed inside the upper housing 20, in threaded engagement thereto, is an actuator 22.

Figure 3:
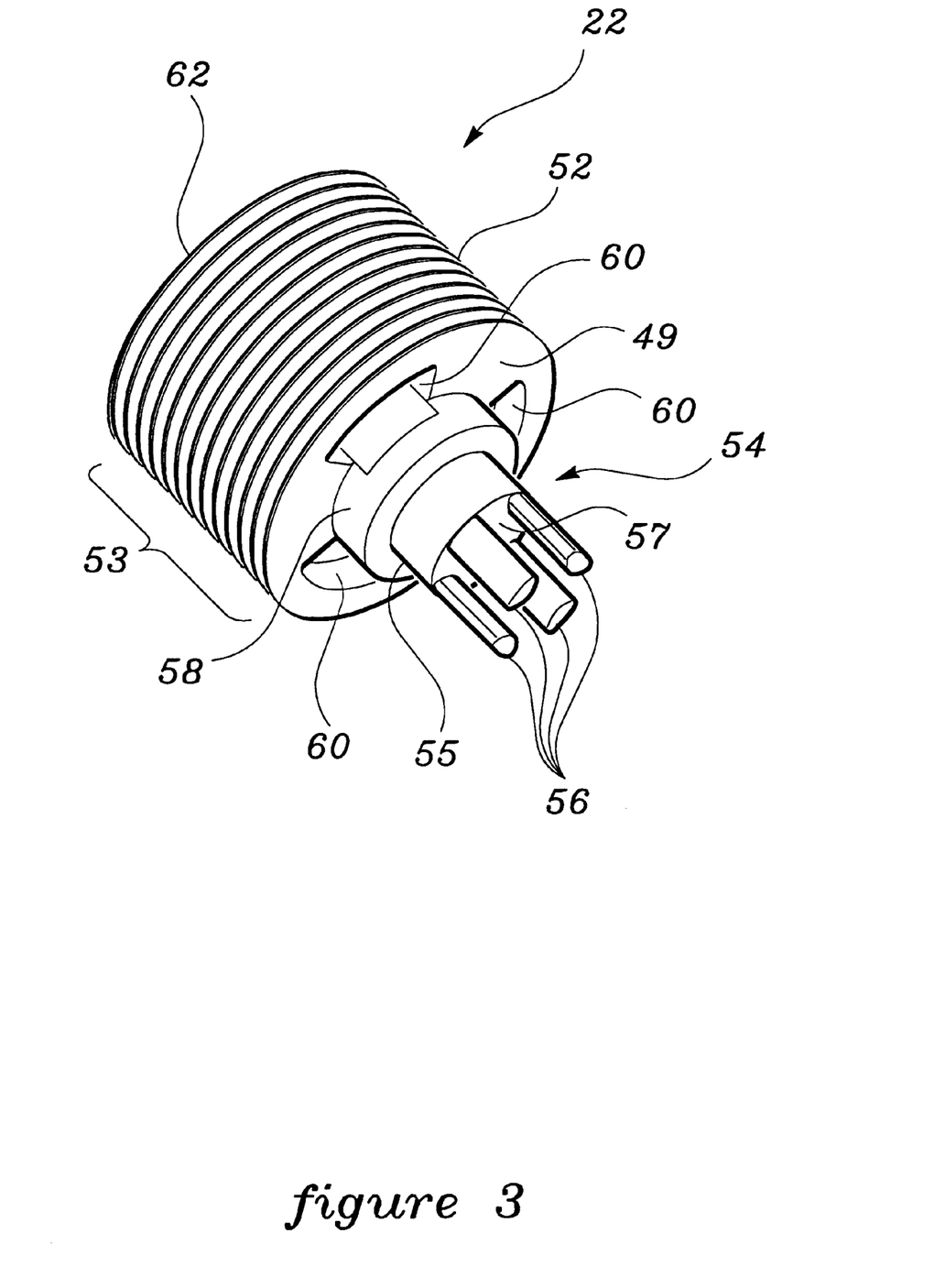
FIG. 3 is a perspective view of the actuating body according to the present invention.

Referring to FIG. 3, actuator 22 comprises a threaded body 52 integrally formed with or attached to an axially extending piston 54. Threaded body 52 forms a tubular interior cavity 62 having an outer surface that forms a series of threads 53 adapted for engagement with threaded portion 46 of upper housing 20. To engage the two components, actuator 22 is inserted through the lower cavity 38 until it engages and meshes with the threads 39 of threaded portion 46. The actuator 22 is then rotated in a clockwise direction until threads 53 are fully engaged to threads 39. In the fully engaged position, the top portion of the threaded body 52 rises slightly above the upper cavity 38. The interior cavity 62 further includes one or more openings 60 that are formed through an actuator base 49 of cavity 62 and spaced around the piston 54. Piston 54 comprises a tubular-shaped piston base 58 at the proximal end thereof that is integrally formed with or attached to a piston rod 55 that is in coaxial alignment with the piston base 58. At the distal end of piston 54 adjacent the piston rod 55 are a plurality of axially extending piston legs 56 that form a circular-shaped void 57 therebetween which extends along the length of legs 56.

Figure 8:
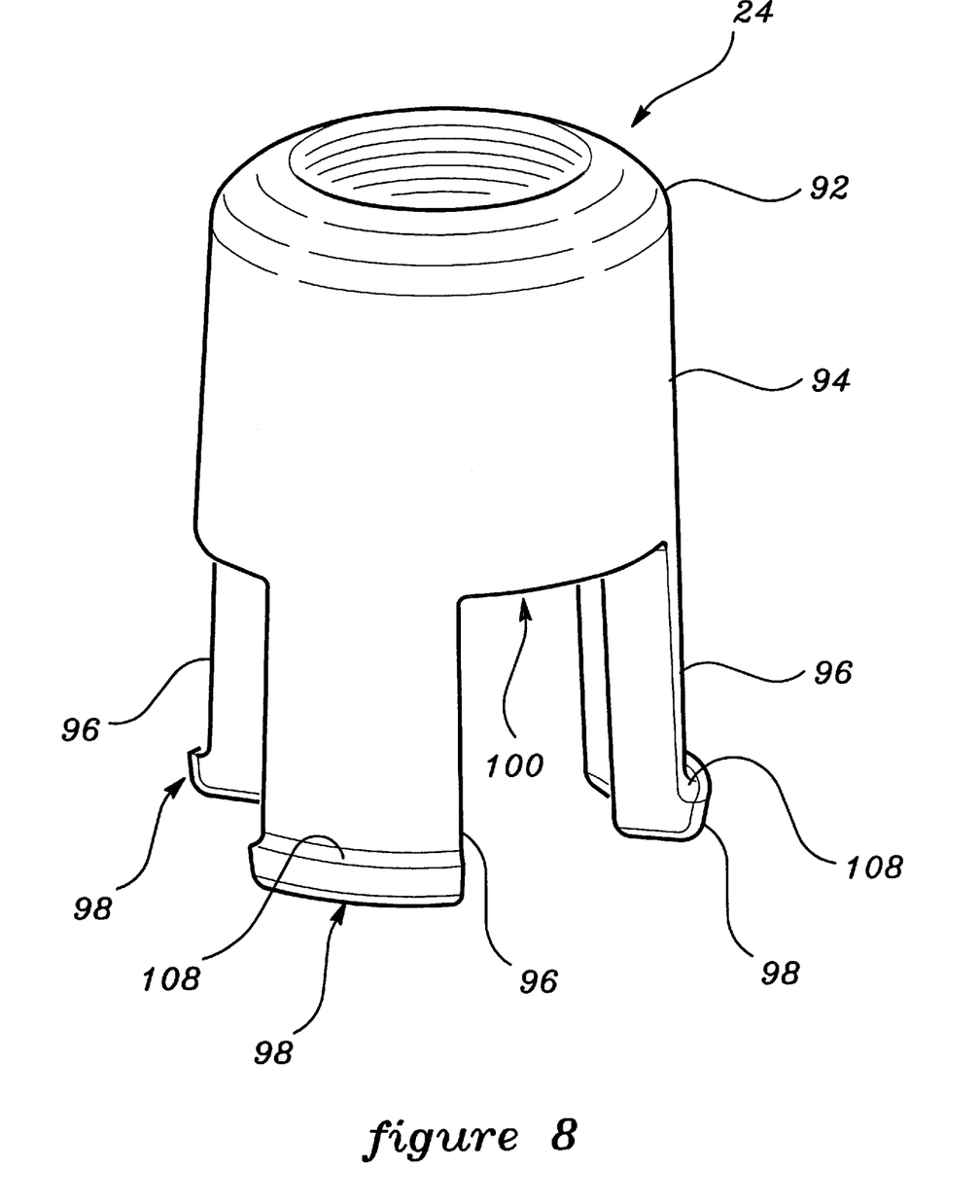
FIG. 8 is a perspective view of the push cap according to the present invention.

Referring to FIGS. 2 and 8, push cap 24 shall be discussed in greater detail. Push cap 24 comprises an upper body 92 and a tubular lower body 94 that forms an inner cavity 100. The lower body 94 has a tubular shape that gradually tapers outward and forms a plurality of cap legs 96 that provide a manual means for actuating valve 10 by a user. Flanges 98 are formed on the free end of each cap leg 96 and extend outward in a generally perpendicular relationship thereto. During assembly of valve 10, the flange 98 of each respective cap leg 96 are inserted through a respective opening 60 of the actuator 22 and includes a retaining edge 108 that is adapted for retention along the peripheral exterior surface area of the actuator base 49 surrounding each opening 60. A spring means 34, interposed between the inner cavity 100 of push cap 24 and the actuator base 49, is provided for biasing the push cap 24 back to its original resting position. Preferably, spring means 34 is manufactured from a resilient polypropylene or acrylic material. Spring means 34 may alternatively be a metal helical spring.

Figure 4:
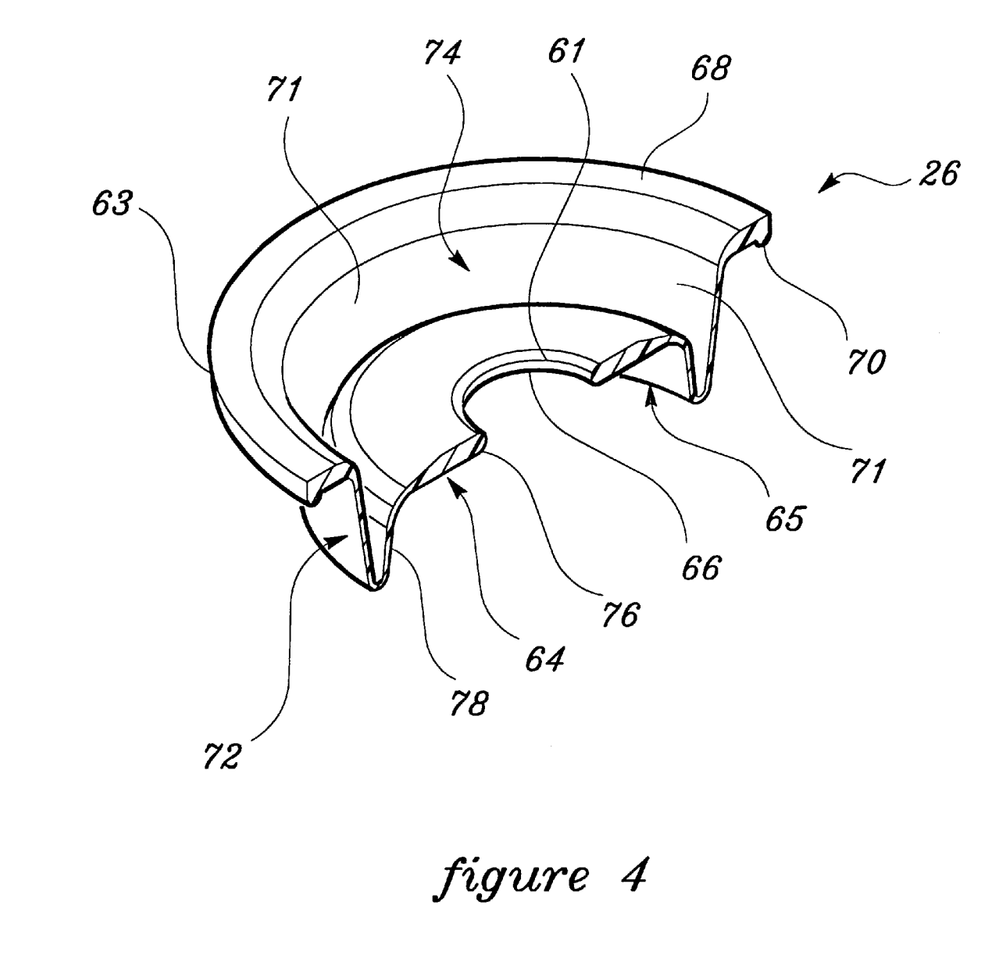
FIG. 4 is a pictorial cut-away of the diaphragm showing the inner periphery and outer periphery according to the present invention.
Figure 9:
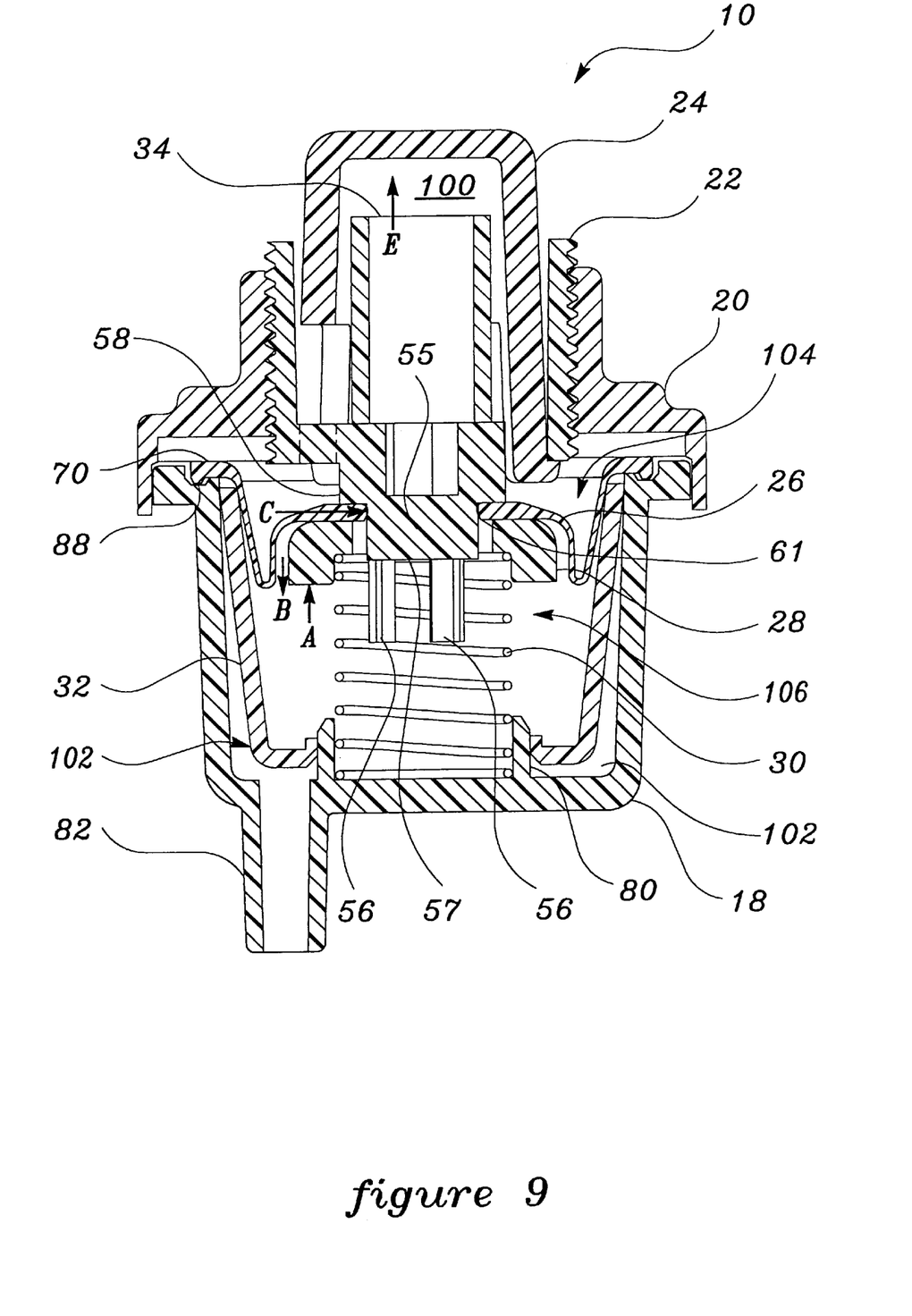
FIG. 9 is a cross section view of the negative pressure relief valve showing the various forces exerted therein according to the present invention.

Referring to FIGS. 4 and 9, the valve 10 further comprises a resilient diaphragm 26 having a diaphragm body 72 that includes an outer periphery 63 that forms the outer edge of body 72 and an inner periphery 61 that forms a co-axial aperture 66 therethrough. Between the inner and outer peripheries 61 and 63 is a diaphragm cavity 74 that forms a recessed area. A protruding latch 70 is included along the circumference of outer periphery 63 for securing and sandwiching the diaphragm body 70 between the lower and upper housings 18 and 20 of valve 10. As illustrated in FIG. 9, the diaphragm body 70 forms a hermetic seal that separates valve 10 into a suction side 106 and a venting side 104. Venting side 104 is the area inside valve 10 that communicates with ambient air while the suction side 106 is the area inside valve 10 and CDU 12 that is maintained at some negative pressure value.

Referring back to FIG. 4, formed inside the diaphragm cavity 74 between the outer periphery 63 and the inner periphery 61 is a platform 64. Platform 64 comprises a raised portion 76 that forms the top section of platform 64 surrounding the aperture 66 and a lower portion 78 that forms a circular interior wall that meets the sidewall 71 of the diaphragm cavity 74. The raised portion 76 forms a platform cavity 65 therein adapted for receiving a retainer 28. The retainer 28 acts as a retaining means for retaining one end of a biasing means 30 and also as a means for spreading out the biasing force along a sufficient surface area of the diaphragm 26. Preferably, the raised portion 76 has a greater material thickness than lower portion 78 in order to provide a greater radial sealing force around the outer circumference of piston 54 by the diaphragm 26 as shall be discussed in greater detail below.

Figure 5:
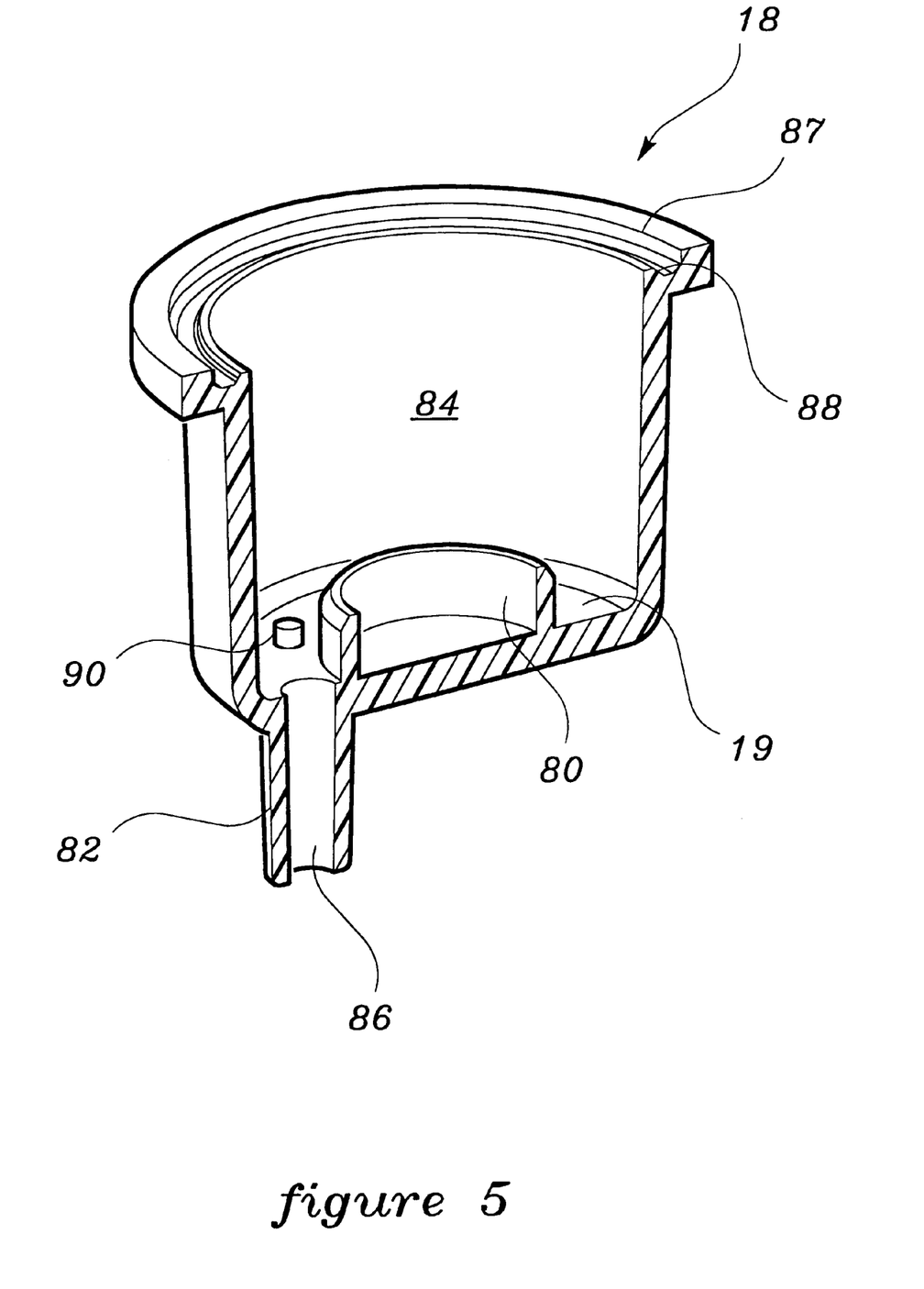
FIG. 5 is a pictorial cut-away of the lower housing according to the present invention.

Referring back to FIG. 2, biasing means 30 is provided in the lower housing 18 for exerting a predetermined force against the diaphragm 26 when negative pressure is maintained at normal levels inside the CDU below the calibration point set for the biasing means 30. As seen in FIG. 5, the lower housing 18 has an annular shape with a bottom portion 19 that comprises a retaining ring 80 adapted for receiving and seating the biasing means 30 therein. Lower housing 18 further comprises a retaining groove 88 formed along the upper edge 87 of the lower housing 18 and is adapted for engagement to the protruding latch 70 of the diaphragm 26 when sandwiching the diaphragm body 72 between the upper and lower housings 18 and 20 in creating the above-noted hermetic seal. At the bottom portion 19 of the lower housing 18 is formed a plurality of supports 90 spaced around the retaining ring 80 for seating a filter 32. A vent 82 comprising a vent channel 86 is formed through the bottom portion 19 that extends away from the lower housing 18 and is in fluid flow communication with the interior of the collection chamber 16. When rising negative pressure inside the CDU 12 reaches the calibration point set for the biasing means 30, ambient air is vented into the suction side 106 of valve 10 through the vent channel 86 and into the collection chamber 16 so as to lower the negative pressure therein.

Preferably, the lower housing 18 is connected to the upper housing 20 by snap fitting the two housings 18 and 20 together by snapping the flange 87 of the lower housing 18 over a plurality of projections (not shown) formed on the inside circumference of the upper housing 20. Once the upper and lower housings 20 and 18 are attached in this manner during manufacturing, the two housings 18 and 20 are preferably ultrasonically welded together, although other suitable means of connecting the two housings 18 and 20 together, such as by interference fit or bonding using an adhesive is felt to fall within the scope of the present invention.

Figure 6:
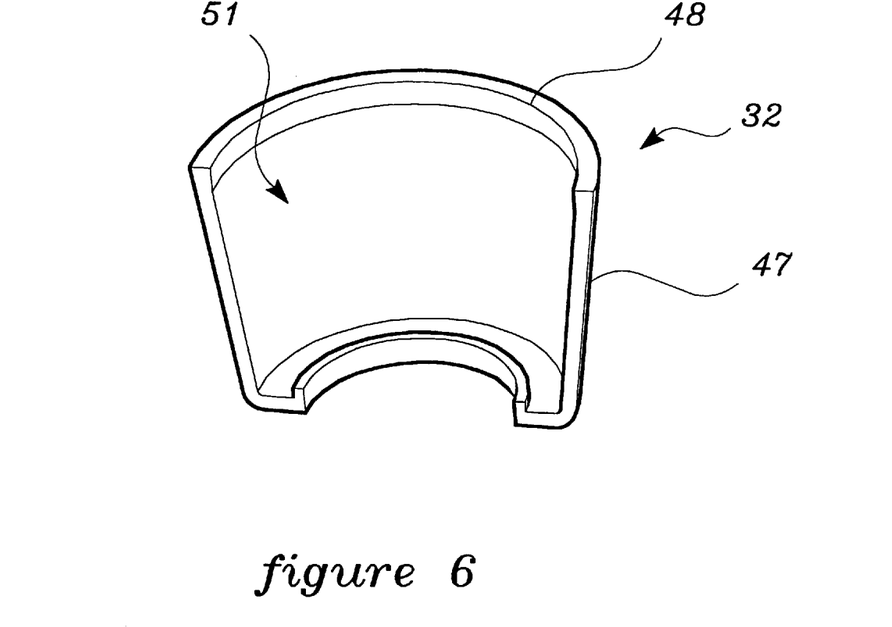
FIG. 6 is a pictorial cut-away of the filter according to the present invention.
Figure 7:
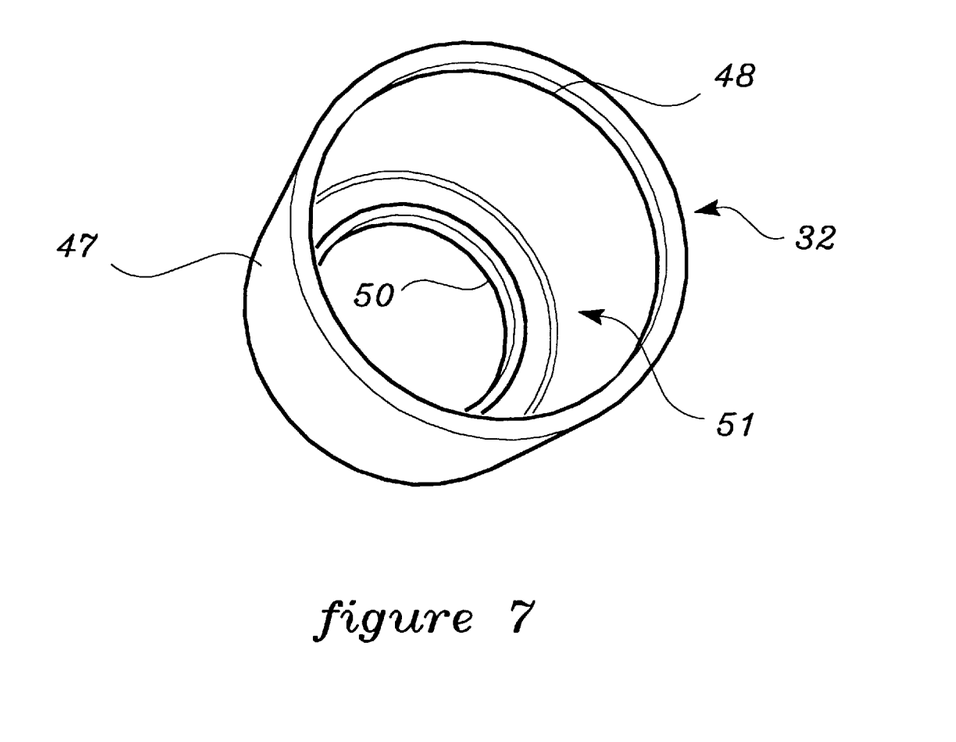
FIG. 7 is a perspective view of the filter according to the present invention.
Figure 10:
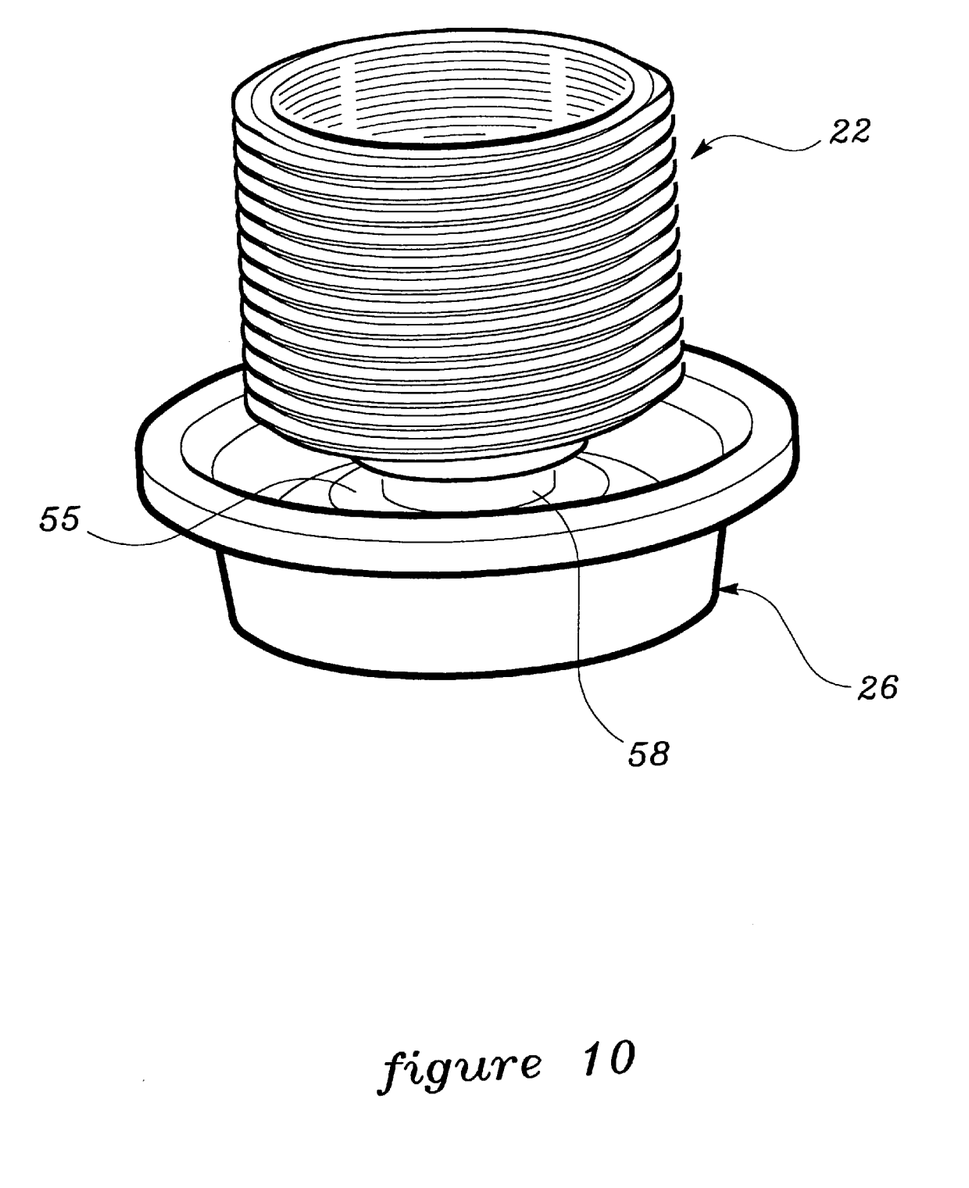
FIG. 10 is a perspective view of the actuating body engaged to the diaphragm showing the diaphragm in the first position according to the present invention.

Referring to FIGS. 6 and 7, filter 32 will be discussed in greater detail. Filter 32 is provided for filtering incoming ambient air of particulate and other contaminants that may be entrained thereto when the valve 10 is open and ambient air is vented into the suction side 106. Filter 32 has a frustoconical shape having an annular wall 47 that defines an interior space 51 and opposed upper and lower openings 48 and 50. As illustrated in FIG. 9, lower opening 50 has a diameter that is approximate to the outside diameter of the retaining ring 80 of the lower housing 18 so that the lower opening 50 engages the ring 80 in an interference fit when filter 32 is seated thereto. Filter 32 is seated down into the retaining ring 80 until it abuts the plurality of supports 90 formed on the bottom portion 19 of the lower housing 18. Supports 90 provide a bottom space 102 between the filter 32 and the bottom portion 19 for unimpeded fluid flow through filter 32 to the venting channel 86. Preferably, filter 32 is constructed of a high density polyethylene with a porosity ranging between 90 and 140 microns. Further, the lower and upper housings 18 and 20 are preferably constructed from a molded acrylic, or in the alternative, a composition made of a blend of Styrene Butadiene and Styrene Acrylic Copolymer. Referring to FIGS. 9–12, the means for actuating the valve 10 and lowering an excess negative pressure condition inside CDU 12 is illustrated. FIG. 10 shows the diaphragm 26 in the first position vis-a-vis the actuator 22 wherein fluid flow communication between the venting side 104 and the suction side 106 of the device is closed. In the first position, the inner periphery 61 of diaphragm 26 is in sealing engagement around the circumference of piston base 55. Referring to FIG. 9, when negative pressure in suction side 106 is below the calibration point set, biasing means 30 applies an axial spring force A against retainer 28 greater than an axial atmospheric force B that is applied against the diaphragm 26 in the opposite direction to force A. Preferably, the spring constant for the biasing means 30 is 0.53 lbs/inch.

When negative pressure inside the CDU 12 begins to rise, the inner periphery 61 of diaphragm 26 will move in sealing engagement around the circumference of the piston 54 toward the piston's 54 free end. As the inner periphery 61 moves in sealing engagement, it applies a constant radial sealing force C about the entire circumference of piston 54 during the movement of the inner periphery 61 along the axis of piston 54. The calibration point for the biasing means 30 is the set value of the force applied by the biasing means 30 against the diaphragm 26 through the retainer 28. When the negative pressure meets or exceeds the calibration point, the inner periphery 61 is brought to the second position where it moves over the plurality of piston legs 56 while still maintaining the constant radial sealing force C around the circumference of piston 54.

Figure 12:
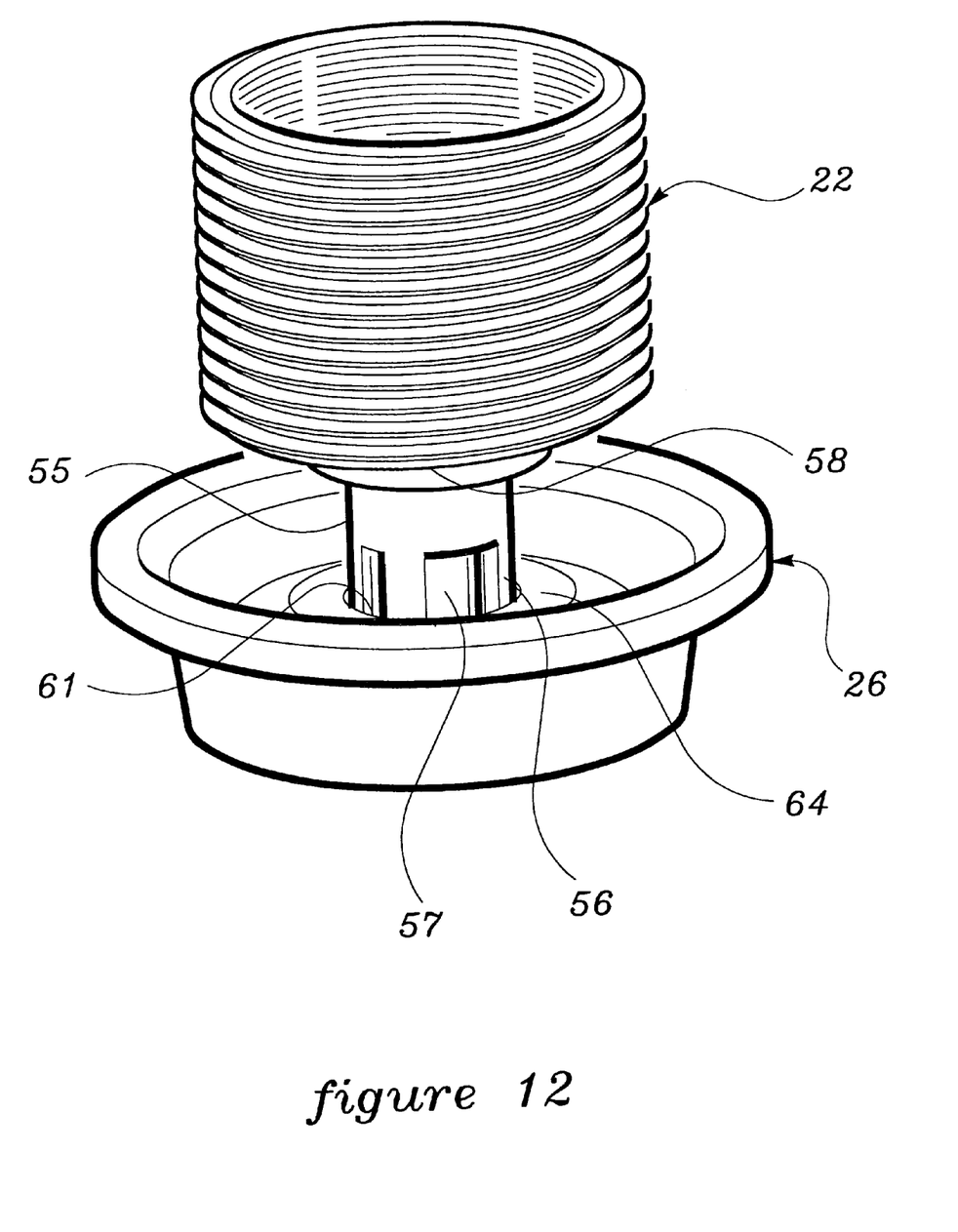
FIG. 12 is a perspective view of the actuating body engaged to the diaphragm showing the diaphragm in the second position according to the present invention.

FIG. 12 shows the diaphragm 26 in the second position vis-a-vis the actuator 22 wherein the inner periphery 61 has moved toward the free end of piston 54, thereby establishing fluid flow communication between the venting side 104 and the suction side 106. In the second position, the inner periphery 61 has moved over the plurality of piston legs 56 and the void 57 formed therebetween has established fluid flow communication between both the venting side 104 and the suction side 106.

Figure 11:
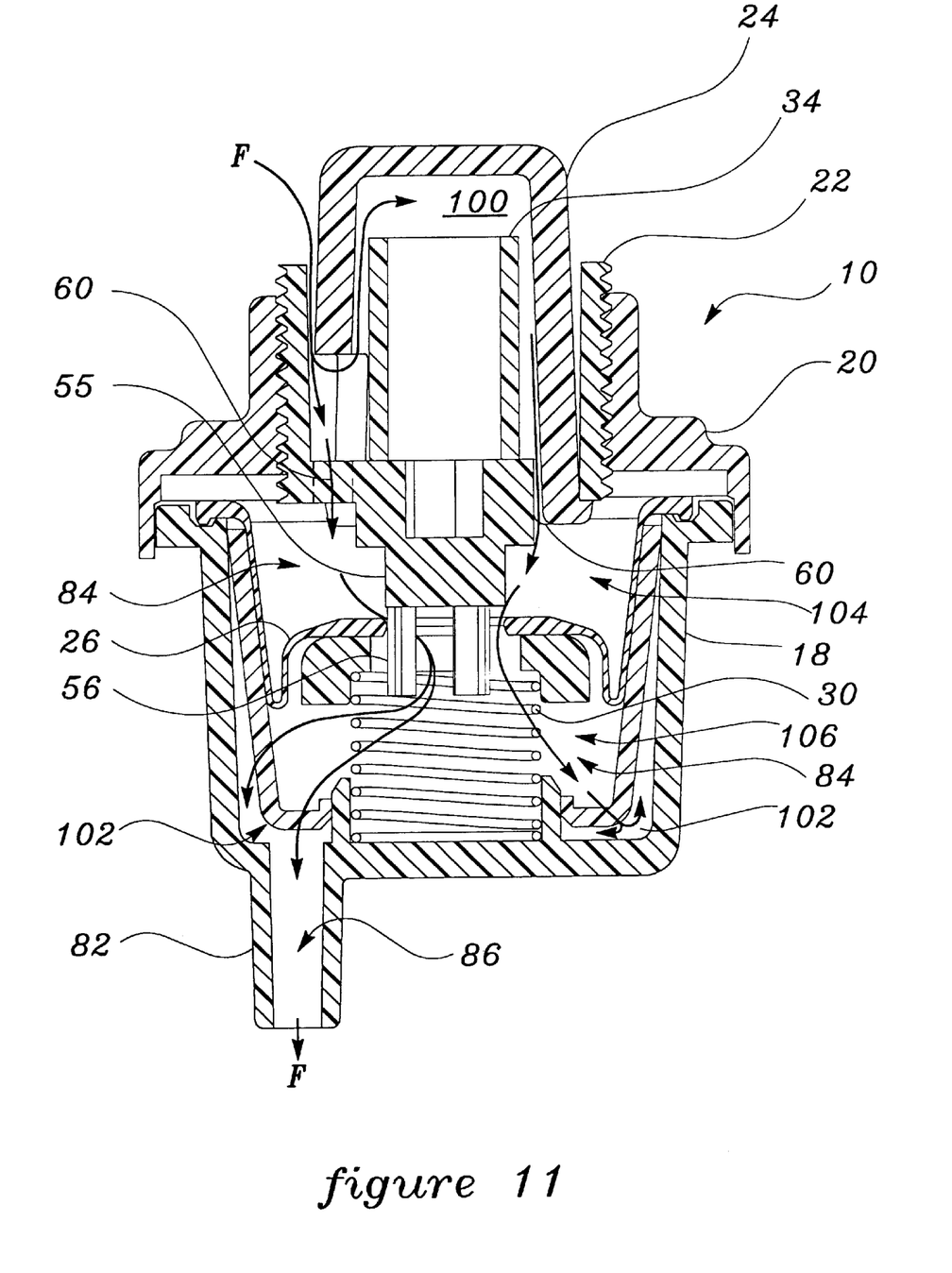
FIG. 11 is a cross section view of the negative pressure relief valve showing the various fluid flows therein according to the present invention.

As illustrated in FIG. 11, when fluid flow communication is established between the two sides 104 and 106, ambient air F is permitted to flow from the venting side 104 to the suction side 106 by following a flow path that runs between the push cap 24 and the cavity 62 and through the openings 60 until it passes through the void 57. Once ambient air F passes through void 57 is filtered through filter 32 and exits through vent 82. The inflow of ambient air flow F causes negative pressure in the suction side 106 to fall until the negative pressure value therein is below the set calibration point, preferably $-70$ cm/$H_2O$.

When negative pressure falls below the calibration point, the axial spring force A applied by the biasing means 30 overcomes the opposing axial atmospheric force B and the inner periphery 61 is forced from the second position to the first position. As the inner periphery 61 returns and sealingly engages around the circumference of the piston rod 55, the void 57 no longer communicates with the venting side 104 and fluid flow communication between the suction side 106 and the venting side 104 is closed.

In manual operation, the user depresses the push cap 24 which forces the retaining flange 98 downward against the diaphragm body 72 so that the inner periphery 61 is moved from the first position to the second position. The user maintains the push cap 24 in its depressed position until negative pressure inside the CDU 12 returns to normal. Once negative pressure returns to normal, the user releases the push cap 24 which causes spring means 34 to exert an axial force E against the surface of the inner chamber 100 and force the push cap 24 to its normal resting position.

Figure 13:
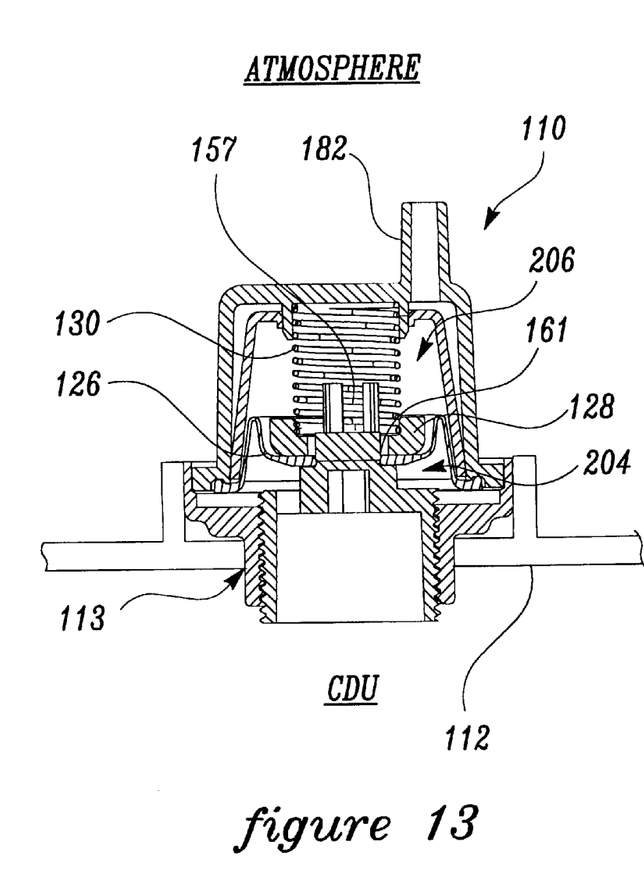
FIG. 13 is a cross section view of an alternative embodiment of the present invention showing the valve oriented as a positive pressure relief valve with the inner periphery of the diaphragm in the first position.

Referring to FIG. 13 an alternative embodiment of the present invention is illustrated. In this embodiment, the valve 110 has the exact same configuration as valve 10 and operates in the same manner except valve 110 does not include the push cap 24 and associated spring means 34 for manual actuation. Further valve 110 is oriented upside down in the outlet 113 of CDU 112, so that the vent 182 is now exposed to atmospheric pressure rather than inside of CDU 112. In this orientation valve 110 acts as a positive pressure relief valve which serves to relieve an positive pressure condition generated inside the interior of CDU 112. In operation, a positive pressure condition that builds up inside CDU 112 will cause the biasing means 130 to apply an axial force against the diaphragm 126 through the retainer 128 as the excess positive pressure inside CDU 112 becomes greater than the atmospheric pressure outside CDU 112. As noted above, when biasing means 130 forces the inner periphery 161 of diaphragm 126 from the first position to the second position as positive pressure inside CDU 112 exceeds the set calibration point for the biasing means 130, the void 157 is placed in fluid flow communication between the venting side 204 and the pressure side 206 of valve 110.

Figure 14:
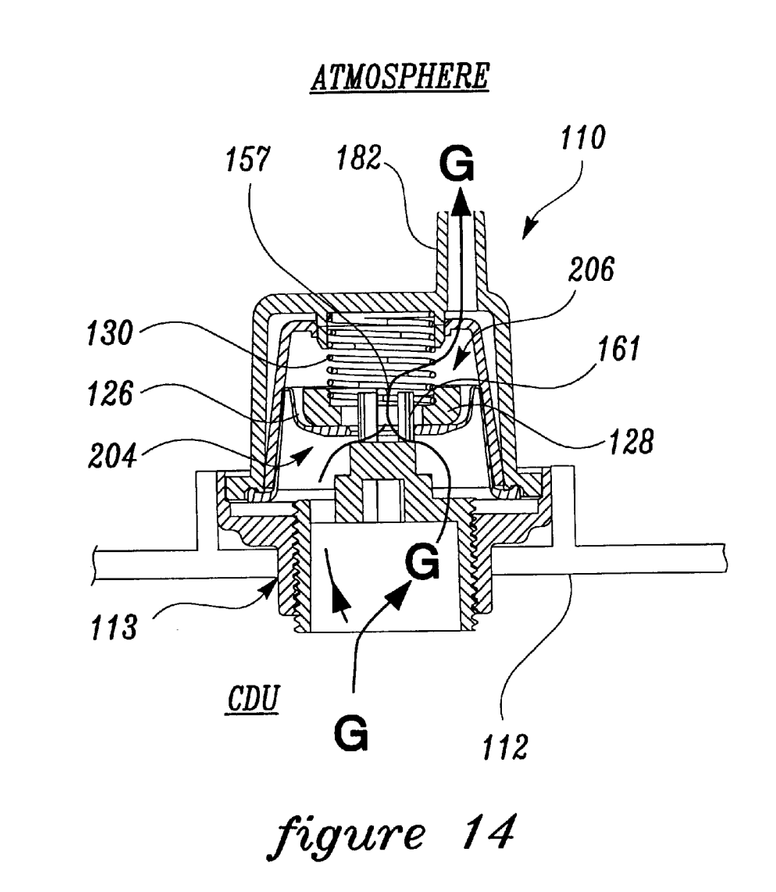
FIG. 14 is a cross-section view of the alternative embodiment of the present invention showing the valve oriented as a positive pressure relief valve with the inner periphery of the diaphragm in the second position.

With the inner periphery 161 in the second position as illustrated in FIG. 14, an air flow G is generated inside CDU 112 as positive pressure therein causes air to flow from the pressure side 204 to the venting side 206 of valve 110 through the void 157 and out to atmosphere through vent 182. Once sufficient air is vented out to atmosphere the positive pressure inside CDU 112 falls below the calibration point set for the biasing means 130, thereby moving the inner periphery 161 back to the first position where fluid flow communication between the venting side 204 and the pressure side 206 is closed therethrough.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

We claim:

1. A pressure relief valve comprising:
  a housing containing a diaphragm body and an actuator, said diaphragm body forming a diaphragm opening, said diaphragm body separating said housing into a venting side and a suction side, said actuator including a piston having a proximal end and a distal end, said piston having a plurality of legs at said proximal end that forms a void therebetween, said piston being adapted for insertion through said diaphragm opening in a first position and a second position, wherein in said first position said diaphragm opening and said proximal end of said piston form an air-tight seal that prevents fluid flow communication between said venting side and said suction, and wherein in said second position said diaphragm opening moves down said piston from its proximal end towards its distal end in response to an increase in negative pressure in said suction, said diaphragm opening maintaining said air-tight seal against said piston until said diaphragm opening travels over a portion of said plurality of legs thereby establishing fluid flow communication between said venting side and said suction side through said void.

2. The valve according to claim 1, wherein said diaphragm opening is maintained in said second position until the negative pressure inside said housing falls below a predetermined threshold so that said diaphragm opening begins to travel back towards the proximal end of said piston to said first position.

3. The valve according to claim 1, wherein in said second position ambient pressure is permitted to enter said suction side and from said venting side.

4. The valve according to claim 1, wherein in said first position said venting side is generally maintained at ambient pressure and said suction side is maintained at a negative pressure.

5. The valve according to claim 1, wherein said actuator body further comprises an interior cavity having an open top portion and a bottom portion, said bottom portion having at least one aperture.

6. The valve according to claim 5, wherein said at least one aperture is in fluid flow communication with said void formed by said plurality of legs when said diaphragm opening is in said second position.

7. The valve according to claim 5, wherein the valve further comprises a push cap, said push cap being partially disposed inside said interior cavity.

8. The valve according to claim 7, wherein said push cap manually shifts said diaphragm opening from said first position to said second position and from said second position to said first position.

9. The valve according to claim 7, wherein said push cap further comprises top portion and a lower portion, said top portion forming an open cavity and said lower portion forming at least one leg adapted for insertion through said at least one aperture of said actuator body, wherein when said push cap manually shifts said diaphragm opening from said first position to said second position said at least one leg is pushing against said diaphragm body through said at least one aperture, thereby forcing said diaphragm opening to travel from said proximal end of said piston to said distal end of said piston.

10. The valve according to claim 7, wherein the valve further comprises a spring means interposed between said push cap and said actuator body, said spring means acting as a biasing force to restore the push cap to its original resting state after a user has pushed said push cap down during manual activation thereof.

11. The valve according to claim 1, wherein the valve further comprises a vent, said vent formed on said housing for venting air when said diaphragm opening is in said second position.

12. The valve according to claim 11, wherein the valve further comprises a filter, said filter disposed inside said housing for filtering air that exits said vent.

13. The valve according to claim 1, wherein when the valve further comprises a spring, said spring applies a predetermined force against said diaphragm body so that said diaphragm opening is placed in said first position.

14. The valve according to claim 13, wherein, said spring is calibrated to a predetermined calibration point so that an increase in negative pressure within said suction side begins to shift said diaphragm opening from said first position to said second position.

15. The valve according to claim 1, wherein said valve further comprises a retainer, said retainer being interposed between said diaphragm body and said spring, wherein said retainer spreads out the force of said spring generally along said diaphragm body.

16. A diaphragm in combination with an actuator contained in a housing for use in a valve comprising:

a diaphragm body including an inner platform integrally formed to an outer flange, said inner platform forming a diaphragm opening therethrough, said outer flange and said inner platform forming a channel therebetween, said diaphragm body separating said housing into a venting side and a suction side; and an actuator body, said actuator body having a top portion and a bottom portion, said top portion forming an interior cavity with an open top, said bottom portion forming an axially extending piston that has a proximal end and a distal end, said piston including a plurality of legs at said proximal end that forms a void therebetween, said piston being adapted for insertion through said diaphragm opening in a first position and a second position, wherein in said first position said diaphragm opening and said proximal end of said piston form a hermetic seal that prevents fluid flow communication between said venting side and said suction side, and wherein in said second position said diaphragm opening travels down said piston from its proximal end to its distal end in response to an increase in negative pressure in said housing, said diaphragm opening maintaining said hermetic seal against said piston until said diaphragm opening moves over a portion of said plurality of legs thereby establishing fluid flow communication between said venting side and said suction side through said void.

17. The combination according to claim 16, wherein said outer flange is secured to the housing in such a manner that an increase in negative pressure causes said inner platform to move axially along said piston in response to said increase in negative pressure while said outer flange remains substantially stationary.

18. The combination according to claim 16, wherein said diaphragm is made from a flexible material that permits said inner platform to flexibly move in a generally axial direction in response to said increase in negative pressure.

19. The combination according to claim 16, wherein said diaphragm opening is maintained in said second position until the negative pressure inside said housing falls below a predetermined threshold so that said diaphragm opening begins to travel back towards the proximal end of said piston to said first position.

20. The valve according to claim 16, wherein in said second position ambient pressure is permitted to enter said suction side from said venting side.

21. The valve according to claim 16, wherein in said first position said venting side is generally maintained at ambient pressure and said suction side is maintained at a negative pressure.

22. The valve according to claim 16, wherein said actuator body further comprises an interior cavity having an open top portion and a bottom portion, said bottom portion having at least one aperture.

23. The valve according to claim 22, wherein said at least one aperture is in fluid flow communication with said void formed by said plurality of legs when said diaphragm opening is in said second position.

24. The valve according to claim 22, wherein the valve further comprises a push cap, said push cap being partially disposed inside said interior cavity.

25. The valve according to claim 24, wherein said push cap manually shifts said diaphragm opening from said first position to said second position and from said second position to said first position.

26. The valve according to claim 24, wherein said push cap further comprises top portion and a lower portion, said top portion forming an open cavity and said lower portion forming at least one leg adapted for insertion through said at least one aperture of said actuator body, wherein when said push cap manually shifts said diaphragm opening from said first position to said second position said at least one leg is pushing against said diaphragm body through said at least one aperture, thereby forcing said diaphragm opening to travel from said proximal end of said piston to said distal end of said piston.

27. The valve according to claim 24, wherein the valve further comprises a spring means interposed between said push cap and said actuator body, said spring means acting as a biasing force to restore the push cap to its original resting state after a user has pushed said push cap down during manual activation thereof.

28. The valve according to claim 16, wherein the valve further comprises a vent, said vent formed on said housing for venting air when said diaphragm opening is in said second position.

29. The valve according to claim 28, wherein the valve further comprises a filter, said filter disposed inside said housing for filtering air that exits said vent.

30. The valve according to claim 16, wherein when the valve further comprises a spring, said spring applies a predetermined force against said diaphragm body so that said diaphragm opening is placed in said first position.

31. The valve according to claim 30, wherein, said spring is calibrated to a predetermined calibration point so that an increase in negative pressure within said suction side begins to shift said diaphragm opening from said first position to said second position.

32. The valve according to claim 16, wherein said valve further comprises a retainer, said retainer being interposed between said diaphragm body and said spring, wherein said retainer spreads out the force of said spring generally along a surface area of said diaphragm body.

33. A pressure relief valve comprising:

a housing having an open top and a vent, said housing forming an interior cavity in communication with said open top and said vent;

an actuator disposed inside said interior cavity, said actuator having a top portion and a bottom portion, said bottom portion having a proximal end and a distal end, said distal end of said bottom portion forming a coaxial piston having a plurality of legs that form a void therebetween; said distal end of said bottom portion forming at least one aperture, said at least one aperture being in communication with said interior cavity;

a diaphragm forming a diaphragm opening adapted to receive said piston therethrough in sealing engagement around said piston, said diaphragm separating said interior cavity into a venting side and a suction side; and a biasing means located in said suction side that is interposed between said housing and said diaphragm, said biasing means applying a predetermined force against said diaphragm in such a manner that said diaphragm opening and said piston form a hermetic seal thereto.

34. The valve according to claim 33, wherein said diaphragm is operable in a first position and a second position, in said first position said diaphragm opening is seated against said piston in a hermetic seal thereto when said negative pressure in said lower chamber is below a predetermined threshold, and in said second position said diaphragm opening travels down said rod until it reaches said plurality of legs so that said venting side is in communication with said suction side through said void in such a manner that negative pressure inside said lower chamber falls below a predetermined threshold thereby causing said biasing means to force said diaphragm opening back to said first position.

* * * * *